US010624883B2

(12) United States Patent
Shimokawa et al.

(10) Patent No.: US 10,624,883 B2
(45) Date of Patent: Apr. 21, 2020

(54) PULMONARY HYPERTENSION PREVENTATIVE OR THERAPEUTIC AGENT CONTAINING COMPONENT EXHIBITING SELENOPROTEIN P ACTIVITY-INHIBITING EFFECT

(71) Applicant: TOHOKU UNIVERSITY, Miyagi (JP)

(72) Inventors: Hiroaki Shimokawa, Miyagi (JP); Kimio Satoh, Miyagi (JP); Nobuhiro Kikuchi, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 16/310,311

(22) PCT Filed: Mar. 28, 2017

(86) PCT No.: PCT/JP2017/012713
§ 371 (c)(1),
(2) Date: Dec. 14, 2018

(87) PCT Pub. No.: WO2017/217071
PCT Pub. Date: Dec. 21, 2017

(65) Prior Publication Data
US 2019/0183882 A1 Jun. 20, 2019

(30) Foreign Application Priority Data

Jun. 17, 2016 (JP) .................................. 2016-121034

(51) Int. Cl.
*A61K 31/4741* (2006.01)
*A61K 31/58* (2006.01)
*A61K 31/215* (2006.01)
*A61P 9/12* (2006.01)
*A61P 11/00* (2006.01)
*A61K 45/00* (2006.01)
*A61K 9/00* (2006.01)

(52) U.S. Cl.
CPC ........ *A61K 31/4741* (2013.01); *A61K 9/0053* (2013.01); *A61K 31/215* (2013.01); *A61K 31/58* (2013.01); *A61K 45/00* (2013.01); *A61P 9/12* (2018.01); *A61P 11/00* (2018.01)

(58) Field of Classification Search
CPC .. A61K 31/4741; A61K 31/58; A61K 31/215; A61K 9/0035; A61P 9/12; A61P 11/00
See application file for complete search history.

(56) References Cited

U.S. PATENT DOCUMENTS

2017/0089924 A1 3/2017 Shimokawa et al.

FOREIGN PATENT DOCUMENTS

JP 2015-63513 4/2015
WO 2015/163098 10/2015

OTHER PUBLICATIONS

Kikuchi et al., Selenoprotein P Promotes Vascular Smooth Cell Proliferation and Pulmonary Hypertension—A Possible Novel Therapeutic Target, European Heart Journal 36(supp. 1): 1206 (1995) (Year: 2015).*
Kikuchi et al., "Selenoprotein p promotes vascular smooth cell proliferation and pulmonary hypertension—a possible novel therapeutic target", European Heart Journal, 36(suppl. 1): 1206 (1995).
Kikuchi et al., "Shinki Byoin Tanpaku Selenoprotein P ni yoru Hai Koketsuatsusho Sokushin Kiko", Respiration and Circulation, 64(5): s28 (2016), cited in the ISR.
Zhang et al., "Ternary polymeric nanoparticles for oral siRNA delivery", Pharm Res, 30(5): 1228-1239 (2013).
Lee et al., "Sanguinarine-induced $G_1$-phase arrest of the cell cycle results from increased p27K1P1 expression mediated via activation of the Ras/ERK signaling pathway in vascular smooth muscle cells", Archives of Biochemistry and Biophysics, 471(2): 224-231 (2008).
Akimova et al., "Cariotonic Steroids Differentially Affect Intracellular $Na^+$ and $[Na^+]i/[K^+]i$-independent Signaling in C7-MDCK Cells", The Journal of Biological Chemistry, 280(1): 832-839 (2005).
Mu et al., "Pristimerin, a Triterpenoid, Inhibits Tumor Angiogenesis by Targeting VEGFR2 Activation", Molecules, 17(6): 6854-6868 (2012).
Jung et al., "Salsalate and Adiponectin Improve Palmitate-Induced Insulin Resistance via Inhibition of Selenoprotein P through the AMPK-FOX01α Pathway", PLOS One, 8(6): e66529 (2013).
Rabinovitch, "Molecular pathogenesis of pulmonary arterial hypertension", Journal of Clinical Investigation, 122(12): 4306-4313 (2012).
Kalogris et al., "Sanguinarine suppresses basal-like breast cancer growth through dihydrofolate reductase inhibition", Biochemical Pharmacology, 90: 226-234 (2014).
Wei et al., "Novel celastrol derivatives inhibit the growth of hepatocellular carcinoma patient-derived xenografts", Oncotarget, 5(14): 5819-5831 (2014).
Satoh et al., "Basigin Mediates Pulmonary Hypertension by Promoting Inflammation and Vascular Smooth Muscle Cell Proliferation", Circulation Research, 115: 738-750 (2014).
Satoh et al., "Statin ameliorates hypoxia-induced pulmonary hypertension associated with down-regulated stromal cell-derived factor-1", Cardiovascular Research, 81: 226-234 (2009).

(Continued)

*Primary Examiner* — Timothy R Rozof

(74) *Attorney, Agent, or Firm* — Wenderoth, Lind & Ponack, L.L.P.

(57) ABSTRACT

A problem to be solved by the present invention is to provide a novel preventive or therapeutic agent for pulmonary hypertension containing as an active ingredient a compound that has not been known for a therapeutic effect on pulmonary hypertension heretofore. The present invention provides a preventive or therapeutic agent for pulmonary hypertension containing an ingredient having a selenoprotein P activity-inhibiting action.

5 Claims, 10 Drawing Sheets

(56) References Cited

OTHER PUBLICATIONS

Satoh et al., "Important Role of Endogenous Erythropoietin System in Recruitment of Endothelial Progenitor Cells in Hypoxia-Induced Pulmonary Hypertension in Mice", Circulation, 113: 1442-1450 (2006).
Shimizu et al., "Crucial Role of ROCK2 in Vascular Smooth Muscle Cells for Hypoxia-Induced Pulmonary Hypertension Mice", Arterioscler Thromb Vasc. Biol, 33: 2780-2791 (2013).
International Search Report dated May 23, 2017 in corresponding International Patent Application No. PCT/JP2017/012713.

* cited by examiner

PULMONARY HYPERTENSION PREVENTATIVE OR THERAPEUTIC AGENT CONTAINING COMPONENT EXHIBITING SELENOPROTEIN P ACTIVITY-INHIBITING EFFECT

CROSS REFERENCE TO RELATED APPLICATION

The present application claims priority from Japanese Patent Application No. 2016-121034 filed on Jun. 17, 2016, the disclosure of which is incorporated herein by reference in its entirety. The present invention relates to a preventive or therapeutic agent for pulmonary hypertension.

TECHNICAL FIELD

Background Art

Pulmonary hypertension is a disease involving increased blood pressure in pulmonary arteries, which carry blood from heart to lungs, leading to impaired cardiac and pulmonary functions, and is a disease quite different from a symptom generally called "hypertension". In addition, pulmonary hypertension is a severe disease with high lethality, and hence there is an urgent need to develop a therapeutic method therefor.

Conventional treatments for pulmonary hypertension include vasodilation treatment using a catheter, and treatment such as surgical removal of thrombus, but less invasive therapeutic methods are desired. In addition, a vasodilator or the like is known as medication (e.g., Non-patent Literature 1), but there are still a large number of patients that cannot be saved by such therapeutic method. Thus, there is a strong demand for further development of a therapeutic agent for pulmonary hypertension.

CITATION LIST

Patent Literature

PTL 1: WO 2015/163098 A1

Non-Patent Literature

NPL 1: J Clin Invest. 2012; 122(12): 4306-4313
NPL 2: Kalogris et al. Biochemical Pharamacology 2014; 90: 226-234
NPL 3: Wei et al. Oncotarget 2014; 5(14): 5819-5831
NPL 4: Satoh et al., Circ. Res. 2014, 115, 738-750.
NPL 5: Satoh et al., Cardiovasc. Res. 2009, 81, 226-234.
NPL 6: Satoh et al., Circulation, 2006, 113, 1442-1450.
NPL 7: Shimizu et al., Arterioscler. Thromb. Vasc. Biol. 2013, 33, 2780-2791.

SUMMARY OF INVENTION

Technical Problem

The present invention provides a novel preventive or therapeutic agent for pulmonary hypertension containing as an active ingredient a compound that has not been known for a therapeutic effect on pulmonary hypertension heretofore.

Solution to Problem

Under such circumstances, the inventors of the present invention have investigated thousands of kinds of compounds. As a result, the inventors have found that some of the compounds each have a selenoprotein P activity-inhibiting action, and that any such compound suppresses excessive proliferation of pulmonary artery smooth muscle cells, which is supposed to be one of the causes for pulmonary hypertension, and has a preventive or therapeutic effect on pulmonary hypertension. The present invention is based on such novel findings.

Thus, the present invention provides the following items:

Item 1. A preventive or therapeutic agent for pulmonary hypertension, including an ingredient having a selenoprotein P activity-inhibiting action.

Item 2. A preventive or therapeutic agent for pulmonary hypertension according to Item 1, wherein the ingredient having a selenoprotein P activity-inhibiting action is at least one kind selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate, or a salt thereof.

Item 3. A preventive or therapeutic agent for pulmonary hypertension according to Item 1 or 2, wherein the preventive or therapeutic agent for pulmonary hypertension includes an orally administered agent.

Item 4. A selenoprotein P activity inhibitor, including at least one kind selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate.

Item 5-1. A method of preventing or treating pulmonary hypertension, including administering an effective dose of an ingredient having a selenoprotein P activity-inhibiting action to an animal.

Item 5-2. A method according to Item 5-1, wherein the ingredient having a selenoprotein P activity-inhibiting action is at least one kind selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate, or a salt thereof.

Item 5-3. A method according to Item 5-1 or 5-2, wherein the administering includes orally administering the ingredient having a selenoprotein P activity-inhibiting action.

Item 6-1. An ingredient having a selenoprotein P activity-inhibiting action, for use in prevention or treatment of pulmonary hypertension.

Item 6-2. An ingredient having a selenoprotein P activity-inhibiting action according to Item 6-1, wherein the ingredient having a selenoprotein P activity-inhibiting action is at least one kind selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate, or a salt thereof.

Item 6-3. An ingredient having a selenoprotein P activity-inhibiting action according to Item 6-1 or 6-2, wherein the prevention or treatment of pulmonary hypertension is performed by orally administering the ingredient having a selenoprotein P activity-inhibiting action.

Item 7-1. A use of an ingredient having a selenoprotein P activity-inhibiting action, for manufacture of a preventive or therapeutic agent for pulmonary hypertension.

Item 7-2. A use according to Item 7-1, wherein the ingredient having a selenoprotein P activity-inhibiting action is at least one kind selected from the group consisting of sanguinarine, bufadienolide, and methyl 10-hydroxy-2,4a, 6a,9,12b,14a-hexamethyl-11-oxo-1,2,3,4,4a,5,6,6a,11,12b, 13,14,14a,14b-tetradecahydropicene-2-carboxylate, or a salt thereof.

Item 7-3. A use according to Item 7-1 or 7-2, wherein the preventive or therapeutic agent for pulmonary hypertension is an orally administered agent.

Item 8-1. A method of inhibiting selenoprotein P activity, including administering an effective dose of at least one kind selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate to an animal.

Item 8-2. A method according to Item 8-1, wherein the administering includes orally administering the at least one kind selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a, 14b-tetradecahydropicene-2-carboxylate.

Item 8-3. A method according to Item 8-1 or 8-2, wherein the animal includes a non-human animal.

Item 8-4. A method according to Item 8-1, wherein the method is performed in vitro.

Item 9-1. At least one kind selected from the group consisting of sanguinarine, bufadienolide, and methyl 10-hydroxy-2,4a,6a,9,12b,14a-hexamethyl-11-oxo-1,2,3,4, 4a,5,6,6a,11,12b,13,14,14a,14b-tetradecahydropicene-2-carboxylate, for use in selenoprotein P activity inhibition.

Item 9-2. At least one kind selected from the group consisting of sanguinarine, bufadienolide, and methyl 10-hydroxy-2,4a,6a,9,12b,14a-hexamethyl-11-oxo-1,2,3,4, 4a,5,6,6a,11,12b,13,14,14a,14b-tetradecahydropicene-2-carboxylate according to Item 9-1, wherein the selenoprotein P activity inhibition is performed by oral administration.

Item 9-3. At least one kind selected from the group consisting of sanguinarine, bufadienolide, and methyl 10-hydroxy-2,4a,6a,9,12b,14a-hexamethyl-11-oxo-1,2,3,4, 4a,5,6,6a,11,12b,13,14,14a,14b-tetradecahydropicene-2-carboxylate according to Item 9-1 or 9-2, wherein the at least one kind is for use in selenoprotein P activity inhibition in a non-human animal.

Item 9-4. At least one kind selected from the group consisting of sanguinarine, bufadienolide, and methyl 10-hydroxy-2,4a,6a,9,12b,14a-hexamethyl-11-oxo-1,2,3,4, 4a,5,6,6a,11,12b,13,14,14a,14b-tetradecahydropicene-2-carboxylate according to Item 9-1, wherein the at least one kind is for use in selenoprotein P activity inhibition in vitro.

Item 10-1. A use of at least one kind selected from the group consisting of sanguinarine, bufadienolide, and methyl 10-hydroxy-2,4a,6a,9,12b,14a-hexamethyl-11-oxo-1,2,3,4, 4a,5,6,6a,11,12b,13,14,14a,14b-tetradecahydropicene-2-carboxylate, for manufacture of a selenoprotein P activity inhibitor.

Item 10-2. A use according to Item 10-1, wherein the selenoprotein P activity inhibitor is an orally administered agent.

Item 10-3. A use according to Item 10-1 or 10-2, wherein the selenoprotein P activity inhibitor includes a selenoprotein P activity inhibitor for a non-human animal.

Item 10-4. A use according to Item 10-1, wherein the selenoprotein P activity inhibitor includes a selenoprotein P activity inhibitor for use in vitro.

Advantageous Effects of Invention

According to the present invention, the novel preventive or therapeutic agent for pulmonary hypertension can be provided by using the ingredient having a selenoprotein P activity-inhibiting action.

BRIEF DESCRIPTION OF DRAWINGS

In FIG. 5, N represents the ratio of non-muscularized vessels, P represents the ratio of partially muscularized vessels, and M represents the ratio of fully muscularized vessels.

DESCRIPTION OF EMBODIMENTS

Figure 1:
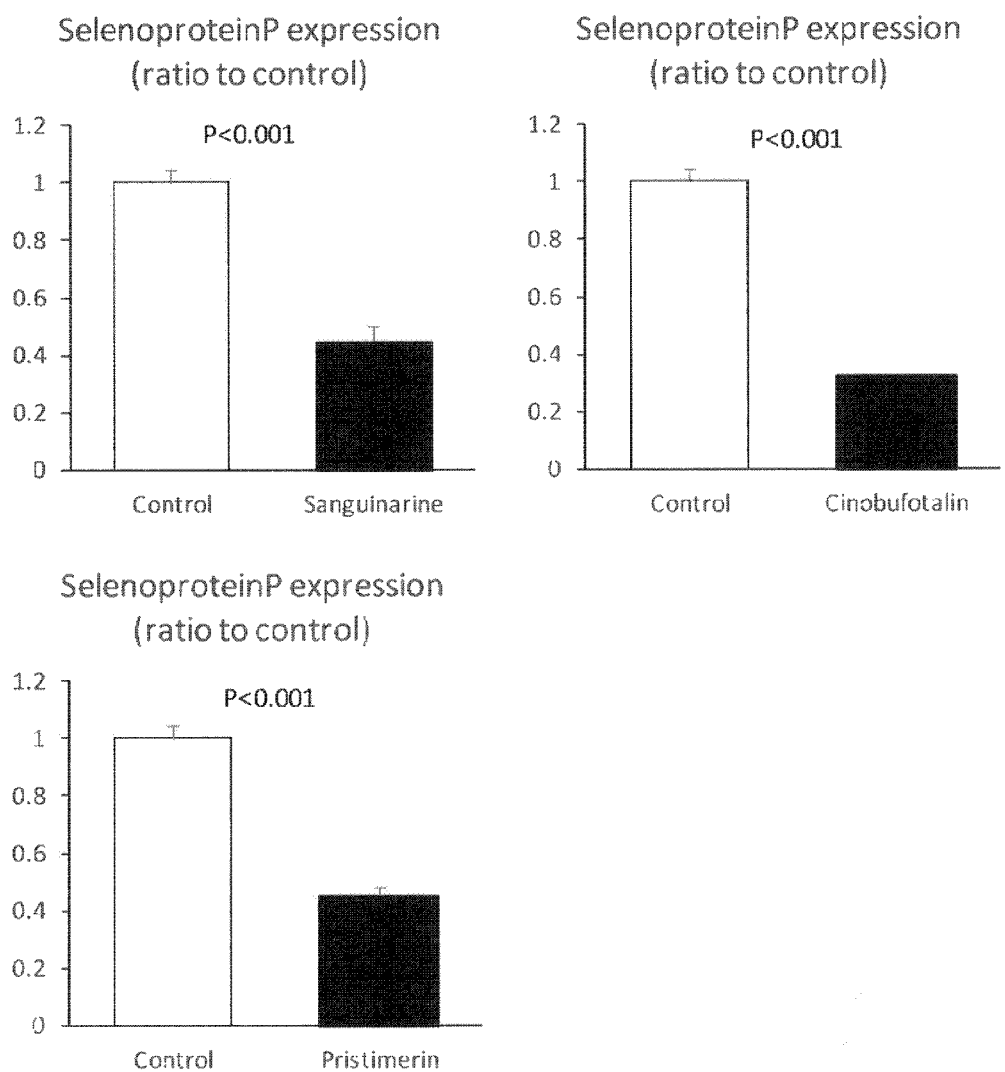
FIG. 1 are graphs for showing selenoprotein P gene expression in Example 1-1.

Preventive or Therapeutic Agent for Pulmonary Hypertension

The present invention provides a preventive or therapeutic agent for pulmonary hypertension containing an ingredient having a selenoprotein P activity-inhibiting action.

Herein, selenoprotein P is a protein most commonly seen in plasma among selenoproteins each containing selenocysteine in the molecule, and has a structure different from those of other selenoproteins, for example, in that selenoprotein P contains 10 selenocysteine residues. In addition, selenoprotein P is considered to be synthesized in the liver. In the present invention, whether or not a certain compound has a selenoprotein P activity-inhibiting action may be identified in conformity with a method described in Example 1-1 of the present application.

A compound that inhibits selenoprotein P activity is, for example, a compound such as sanguinarine, bufadienolide, and methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate, or a salt thereof. Herein, the compound that inhibits selenoprotein P activity, such as sanguinarine, bufadienolide, and methyl 10-hydroxy-2,4a, 6a,9,12b,14a-hexamethyl-11-oxo-1,2,3,4,4a,5,6,6a,11,12b, 13,14,14a,14b-tetradecahydropicene-2-carboxylate, is sometimes simply abbreviated as "compound A". Accordingly, the present invention provides a preventive or therapeutic agent for pulmonary hypertension containing a compound A or a salt thereof.

Sanguinarine or a salt (e.g., a chloride) thereof serving as an active ingredient of the present invention is a compound having the following structure or a salt thereof, and is a known substance:

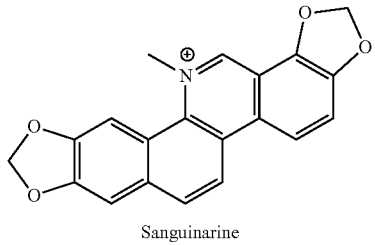 [SMILES: C[n+]1cc2c3c(ccc2c2ccc4cc5c(cc4c21)OCO5)OCO3]
Sanguinarine

Sanguinarine has heretofore been studied as a therapeutic drug for a malignant tumor (Non-patent Literature 2). However, no previous study has reported that sanguinarine inhibits selenoprotein P activity or has a preventive or therapeutic effect on pulmonary hypertension. Accordingly, the effect of the present invention is unpredictable from the related art.

Herein, bufadienolide serving as an active ingredient of the present invention is a generic name for steroids each having a basic skeleton represented by the following formula (I-A) or (II-A):

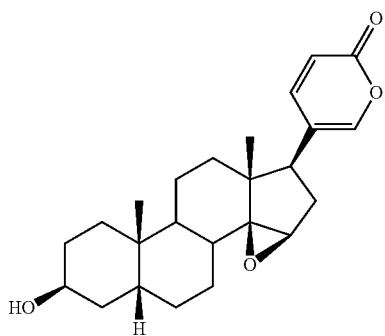
(I-A)

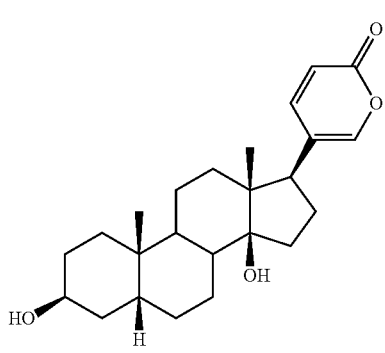
(II-A)

For example, bufadienolide or a salt thereof is, for example, a compound represented by the following formula (I) or (II), and is preferably a compound represented by the formula (I) or a salt thereof:

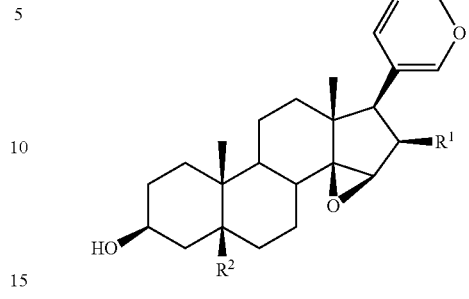
(I)

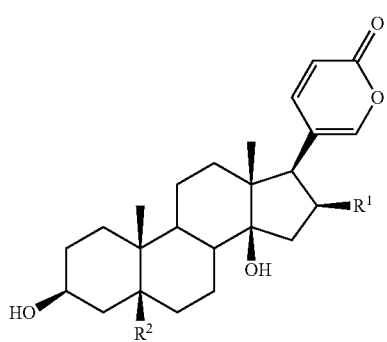
(II)

where $R^1$ represents hydrogen, a hydroxy group, or an acetyloxy group, and $R^2$ represents hydrogen or a hydroxy group.

More specifically, bufadienolide or the salt thereof is preferably exemplified by compounds having the following structures or salts thereof:

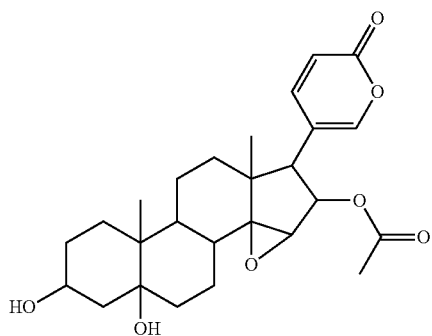

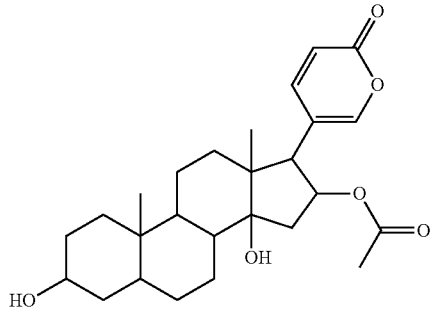

-continued

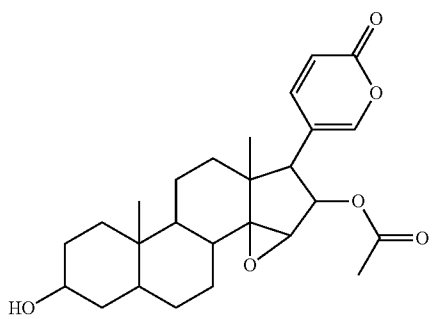

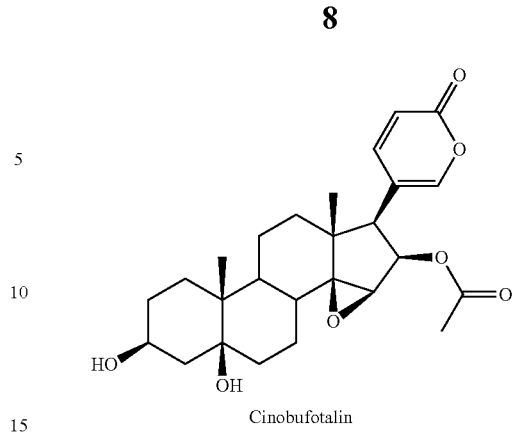
Cinobufotalin

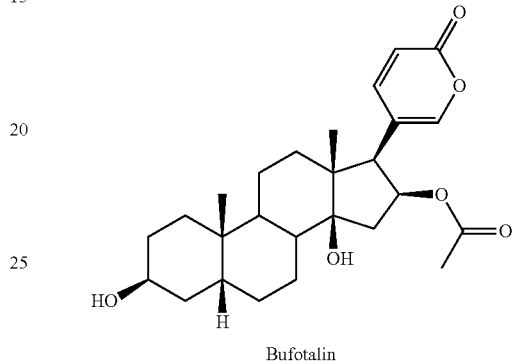
Bufotalin

Of those compounds, 5a,7-dihydroxy-9a,11a-dimethyl-1-(2-oxo-2H-pyran-5-yl)hexadecahydronaphtho[1',2':6,7]indeno[1,7a-b]oxiren-2-yl acetate represented by:

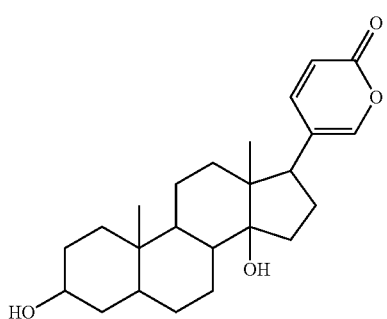

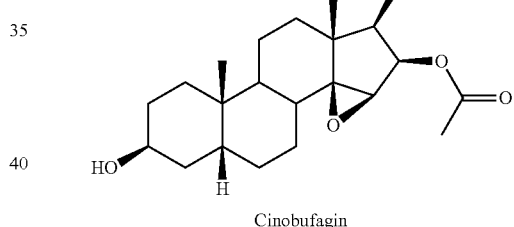
Cinobufagin

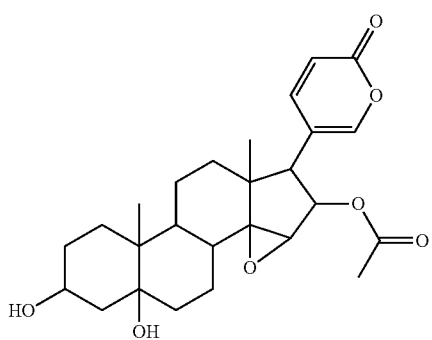 [SMILES: CC(=O)OC1C(c2ccc(=O)oc2)C2(C)CCC3C(CCC4(O)CC(O)CCC34C)C23OC13]

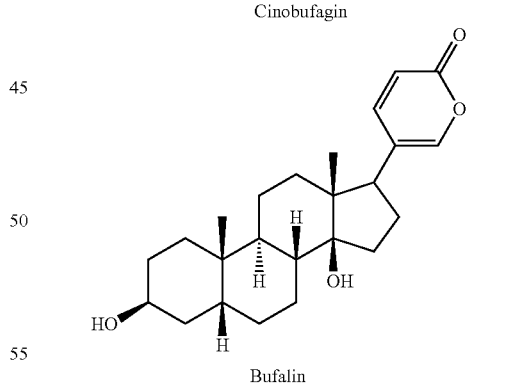
Bufalin is preferred.

More specifically, there are given, for example, cinobufotalin (CAS 1108-68-5, [(1R,2R,2aR,3aS,5aS,7S,9aR,11aR)-5a,7-dihydroxy-9a,11a-dimethyl-1-(2-oxo-2H-pyran-5-yl)hexadecahydronaphtho[1',2':6,7]indeno[1,7a-b]oxiren-2-yl acetate]), bufotalin, cinobufagin, and bufalin having the following structures:

Of those compounds or salts thereof, cinobufotalin or a salt thereof is preferred. Bufadienolide or the salt thereof may be a known substance, or may be appropriately produced from the known substance.

Bufadienolide is a steroid isolated from secretions from the parotid and sebaceous glands of a toad. Such secretions from the parotid and sebaceous glands of a toad are used as cardiac diuretics. However, no previous study has reported that bufadienolide inhibits selenoprotein P activity or has a preventive or therapeutic effect on pulmonary hypertension. Accordingly, the effect of the present invention is unpredictable from the related art.

Methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate or a salt thereof serving as an active ingredient of the present invention is a known compound having the following structure or a salt thereof:

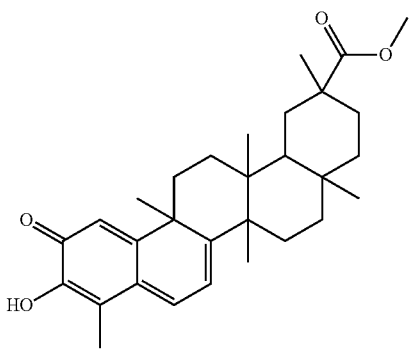 [SMILES: COC(=O)C1(C)CCC2(C)CCC3(C)C4=CC=C5C(=CC(=O)C(O)=C5C)C4(C)CCC3(C)C2C1]

In the present invention, methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate is sometimes simply referred to as "compound P".

Of the compounds P, pristimerin (CAS 1258-84-0 [methyl (2R,4aS,6aS,12bR,14aS,14bR)-10-hydroxy-2,4a,6a,9,12b,14a-hexamethyl-11-oxo-1,2,3,4,4a,5,6,6a,11,12b,13,14,14a,14b-tetradecahydropicene-2-carboxylate]) having the following structure is preferred:

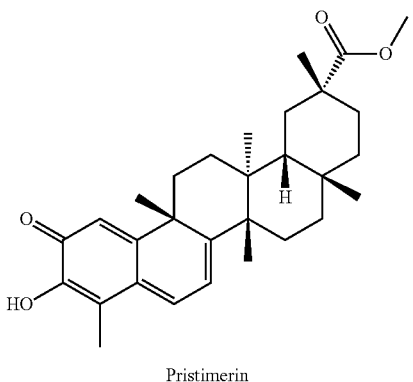

Pristimerin

The compound P has heretofore been studied as a therapeutic drug for a malignant tumor (Non-patent Literature 3). However, no previous study has reported that the compound P inhibits selenoprotein P activity or has a preventive or therapeutic effect on pulmonary hypertension. Accordingly, the effect of the present invention is unpredictable from the related art.

The inventors of the present invention have found that sanguinarine, cinobufotalin, and pristimerin exhibiting selenoprotein P activity-inhibiting actions are all effective for prevention or treatment of pulmonary hypertension. Accordingly, although sanguinarine, cinobufotalin, and pristimerin, or salts thereof are preferred compounds, it is conceivable that any other compound that inhibits selenoprotein P activity is also similarly effective for prevention or treatment of pulmonary hypertension. Although it is not clear how the selenoprotein P activity-inhibiting action is associated with the prevention or treatment of pulmonary hypertension, for example, a possible mechanism is as follows: the compound that inhibits selenoprotein P activity suppresses the proliferation of pulmonary hypertension-derived pulmonary artery smooth muscle cells (in actuality, the above-mentioned three compounds all exhibit suppressive effects on the proliferation of human pulmonary hypertension-derived pulmonary artery smooth muscle cells) to suppress pulmonary vascular remodeling in pulmonary hypertension, to thereby exhibit a therapeutic effect. The inventors of the present invention have already found that pulmonary hypertension can be tested by using as an indicator the concentration of selenoprotein P protein in a sample derived from a subject, that is, selenoprotein P protein can be used as a biomarker for detecting pulmonary hypertension (Patent Literature 1). In general, however, a wide variety of factors are often involved in the development and progress of a certain disease. Therefore, even when one factor is blocked, a desired therapeutic effect is not necessarily obtained. Accordingly, even when treatment using a biomarker for detecting a certain disease as a target for treating the disease is attempted, a preferred result is not necessarily obtained.

In addition, a cause for pulmonary hypertension serving as a target disease of the present invention has not been sufficiently clarified. Besides, how the selenoprotein P activity is specifically involved in pulmonary hypertension has also not been clarified. Accordingly, the novel finding by the inventors of the present invention that the ingredient having a selenoprotein P activity-inhibiting action has been effective for prevention or treatment of pulmonary hypertension is unpredictable from the related art.

In the present invention, examples of the compound A include: low-molecular-weight compounds (e.g., compounds having molecular weights of 5,000 or less, preferably 2,000 or less, more preferably 1,000 or less, still more preferably 500 or less), such as sanguinarine, bufadienolide, and the compound P, or salts thereof; and high-molecular-weight compounds (compounds having molecular weights higher than those of the above-mentioned low-molecular-weight compounds, such as compounds having molecular weights of more than 500, preferably more than 1,000, more preferably more than 2,000, still more preferably more than 5,000), such as a nucleic acid and an antibody. When the low-molecular-weight compound is used as the compound A, the low-molecular-weight compound is preferably, for example, sanguinarine, bufadienolide, and the compound P, or a salt thereof, more preferably, for example, sanguinarine or bufadienolide, or a salt thereof, still more preferably, for example, sanguinarine or a salt thereof.

In addition, when the compound A or the salt thereof serving as the active ingredient of the present invention has an isomer, such as an optical isomer, a stereoisomer, or a regioisomer, the present invention may encompass both of an invention using any of the isomers and an invention using a mixture of a variety of isomers, unless it is clearly specified which of the isomers is used.

The salt of the compound A serving as the active ingredient of the present invention encompasses an acid addition salt and a salt with a base. Specific examples of the acid addition salt include: inorganic acid salts, such as a hydrochloride, a hydrobromide, a hydroiodide, a sulfate, a perchlorate, and a phosphate; organic acid salts, such as an oxalate, a malonate, a succinate, a maleate, a fumarate, a lactate, a malate, a citrate, a tartrate, a benzoate, a trifluoroacetate, an acetate, a methanesulfonate, a p-toluenesulfonate, and a trifluoromethanesulfonate; and acidic amino acid salts, such as a glutamate and an aspartate. Specific examples of the salt with a base include: alkali metal or alkaline earth metal salts, such as a sodium salt, a potassium salt, and a calcium salt; salts with organic bases, such as a pyridine salt and a triethylamine salt; and salts with basic amino acids, such as lysine and arginine. In addition, when the compound A serving as the active ingredient of the present invention is a cation, the salt of the compound A also encompasses a halide (e.g., a chloride) and the like.

The compound A serving as the active ingredient of the present invention may be present in the form of a hydrate or a solvate, and hence the compound A serving as the active ingredient of the present invention also encompasses such hydrate and solvate.

A solvent forming the solvate is exemplified by alcohols, such as ethanol and propanol, organic acids, such as acetic acid, esters, such as ethyl acetate, ethers, such as tetrahydrofuran and diethyl ether, ketones, such as acetone, and DMSO.

In the present invention, the compound A or the salt thereof serving as the active ingredient of the present invention may be used alone as a preventive or therapeutic agent for pulmonary hypertension, or may be used as a pharmaceutical composition in combination with any of various pharmaceutically acceptable carriers (e.g., a tonicity agent, a chelating agent, a stabilizing agent, a pH regulator, a preservative, an antioxidant, a solubilizing agent, or a thickening agent).

Examples of the tonicity agent include: sugars, such as glucose, trehalose, lactose, fructose, mannitol, xylitol, and sorbitol; polyhydric alcohols, such as glycerol, polyethylene glycol, and propylene glycol; and inorganic salts, such as sodium chloride, potassium chloride, and calcium chloride. Those tonicity agents may be used alone or in combination thereof.

Examples of the chelating agent include: edentates, such as disodium edetate, calcium disodium edetate, trisodium edetate, tetrasodium edetate, and calcium edetate; ethylenediaminetetraacetate; nitrilotriacetic acid or salts thereof; sodium hexametaphosphate; and citric acid. Those chelating agents may be used alone or in combination thereof.

An example of the stabilizing agent is sodium hydrogen sulfite.

Examples of the pH regulator include acids, such as hydrochloric acid, carbonic acid, acetic acid, and citric acid, and also include: alkali metal hydroxides, such as sodium hydroxide and potassium hydroxide; alkali metal carbonates or hydrogen carbonates, such as sodium carbonate; alkali metal acetates, such as sodium acetate; alkali metal citrates, such as sodium citrate; and bases, such as trometamol. Those pH regulators may be used alone or in combination thereof.

Examples of the preservative include: sorbic acid; potassium sorbate; parahydroxybenzoates, such as methyl parahydroxybenzoate, ethyl parahydroxybenzoate, propyl parahydroxybenzoate, and butyl parahydroxybenzoate; quaternary ammonium salts, such as chlorhexidine gluconate, benzalkonium chloride, benzethonium chloride, and cetylpyridinium chloride; alkylpolyaminoethylglycine; chlorobutanol; polyquad; polyhexamethylene biguanide; and chlorhexidine. Those preservatives may be used alone or in combination thereof.

Examples of the antioxidant include sodium hydrogen sulfite, dried sodium sulfite, sodium pyrosulfite, and concentrated mixed tocopherols. Those antioxidants may be used alone or in combination thereof.

Examples of the solubilizing agent include sodium benzoate, glycerin, D-sorbitol, glucose, propylene glycol, hydroxypropyl methylcellulose, polyvinylpyrrolidone, macrogol, and D-mannitol. Those solubilizing agents may be used alone or in combination thereof.

Examples of the thickening agent include polyethylene glycol, methyl cellulose, ethyl cellulose, carmellose sodium, xanthan gum, sodium chondroitin sulfate, hydroxyethyl cellulose, hydroxypropyl cellulose, hydroxypropyl methylcellulose, polyvinylpyrrolidone, and polyvinyl alcohol. Those thickening agents may be used alone or in combination thereof.

In addition, the pharmaceutical composition may further contain, in addition to the compound A or the salt thereof, a compound known to have a preventive or therapeutic action on pulmonary hypertension. Examples of the compound known to have a preventive or therapeutic action on pulmonary hypertension include epoprostenol, sildenafil, and bosentan. Those compounds may be used alone or in combination thereof.

In the embodiment of the pharmaceutical composition, the content of the compound A or the salt thereof in the composition is not particularly limited, and may be appropriately set within, for example, conditions such as 90 mass % or more, 70 mass % or more, 50 mass % or more, 30 mass % or more, 10 mass % or more, 5 mass % or more, and 1 mass % or more in terms of the content of the compound A.

A dosage form is not particularly limited, and examples thereof may include various dosage forms including: orally administered agents, such as a tablet, a pill, a capsule, a powder, a granule, and a syrup; and parenterally administered agents, such as an injection (e.g., intravenous injection, intramuscular injection, or local injection), a gargle, a drop, external preparations (an ointment, a cream, a patch, and an inhalant), and a suppository. Of the dosage forms, for example, orally administered agents (e.g., a tablet, a pill, a capsule, a powder, a granule, and a syrup) and external preparations (an ointment, a cream, a patch, and an inhalant) are preferred.

In the present invention, the dose of the compound A or the salt thereof varies depending on, for example, an administration route and the age, body weight, or symptom of a patient, and hence cannot be uniquely defined. However, the dose only needs to be such an amount that a daily dose for adults is generally about 5,000 mg or less, preferably about 1,000 mg or less, more preferably 500 mg or less in terms of the dose of the compound A. The lower limit of the dose of the compound A or the salt thereof is also not particularly limited, and may be appropriately set within, for example, such a range that a daily dose for adults is generally 1 mg or more, preferably 10 mg or more, more preferably 100 mg or more in terms of the dose of the compound A. When administered once daily, the compound A or the salt thereof only needs to be contained in the above-mentioned amount in a single dose. When administered three times daily, the compound A or the salt thereof only needs to be contained in an amount corresponding to one-third of the above-mentioned amount in a single dose.

The preventive or therapeutic agent for pulmonary hypertension of the present invention is administered to patients, such as mammals. Examples of the mammals include humans, monkeys, mice, rats, rabbits, cats, dogs, pigs, cattle, horses, and sheep.

The preventive or therapeutic agent for pulmonary hypertension of the present invention prevents or treats and ameliorates pulmonary hypertension by at least suppressing excessive proliferation of pulmonary artery smooth muscle cells. Accordingly, the present invention also provides a suppressor for excessive proliferation of pulmonary artery smooth muscle cells containing a compound A or a salt thereof. The active ingredient, dosage form, dose, and the like of the suppressor for excessive proliferation of pulmonary artery smooth muscle cells are the same as those of the preventive or therapeutic agent for pulmonary hypertension.

Selenoprotein P Activity Inhibitor

The present invention also provides a selenoprotein P activity inhibitor containing at least one kind selected from the group consisting of sanguinarine, bufadienolide, and a compound P, or a salt thereof. The active ingredient, dosage form, dose, and the like of the selenoprotein P activity inhibitor are the same as those of the preventive or therapeutic agent for pulmonary hypertension.

As mentioned above, it has not been known that sanguinarine, bufadienolide, and the compound P, or the salts thereof each exhibit selenoprotein P-inhibiting activity, and this is the novel finding by the inventors of the present invention. As mentioned above, the selenoprotein P activity can be suppressed by using at least one kind selected from the group consisting of sanguinarine, bufadienolide, and the compound P. Accordingly, the selenoprotein P activity inhibitor according to the present invention can be used as a preventive or therapeutic agent for a disease that may be treated by selenoprotein P activity suppression. Examples of the disease that may be treated by selenoprotein P activity suppression include, but not particularly limited to, diabetes mellitus, such as type II diabetes mellitus.

The present invention is more specifically described below by way of Examples. However, the present invention is not limited thereto.

EXAMPLES

Example 1-1

To pulmonary arterial hypertension-derived pulmonary artery smooth muscle cells cultured in a standard medium containing 10% fetal bovine serum (FBS), sanguinarine (2 mM solution prepared by dissolving a product available from SSX (Cat. No. 1845, Sanguinarine Chloride 10 mg) in 100% dimethyl sulfoxide (DMSO)), cinobufotalin (2 mM solution prepared by dissolving a product available from Sigma (Cat. No. C1147-10MG, Cinobufotalin 10 mg) in 100% DMSO), and pristimerin (2 mM solution prepared by dissolving a product available from RSD (Cat. No. 3731/50, Pristimerin 50 mg) in 100% DMSO) were each added so that its final concentration was 5 µM, and the cells were cultured for 24 hours (n=4 per group).

After the culture for 24 hours, total RNA was extracted and purified from those cells, and a change in selenoprotein P gene expression was compared to that of a control group (10% FBS standard medium containing DMSO at the same concentration) by RT-PCR. Values each normalized to a glyceraldehyde-3-phosphate dehydrogenase (GAPDH) internal control were used as values for the selenoprotein P gene expression.

The results are as shown in FIG. 1. When any of the compounds was administered, the selenoprotein P gene expression in the pulmonary artery smooth muscle cells was significantly suppressed (when any of the compounds was administered, the selenoprotein P gene expression showed a statistically significant difference from that of the control).

Example 1-2

Figure 2:
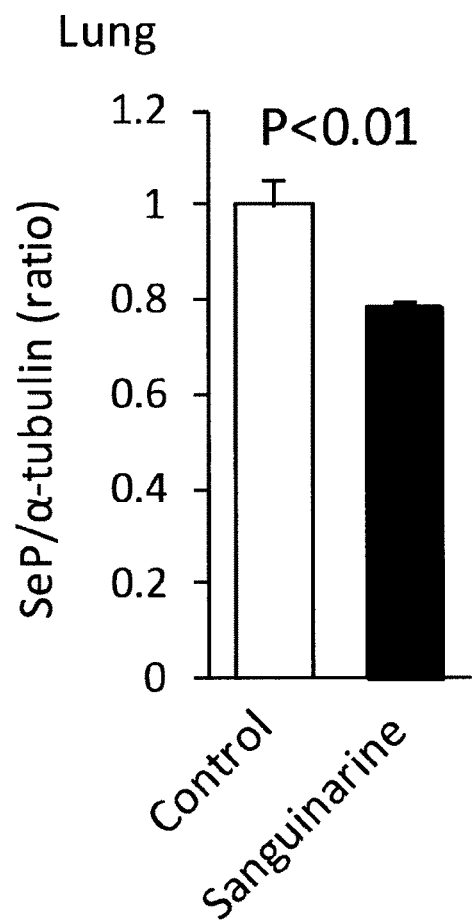
FIG. 2 is a graph for showing the results of Western blotting in Example 1-2.

In addition, regarding sanguinarine, C57BL/6 mice (n=8 per group) were administered sanguinarine (5 mg/kg/day, daily for 28 days, oral administration). At the same time, the mice were bred under a 10% hypoxic environment. Thus, a hypoxia-induced pulmonary hypertension mouse model was generated and investigated. The results of Western blotting were as follows: the selenoprotein P protein expression in the lungs was significantly suppressed in the sanguinarine administration group as compared to the control (FIG. 2).

Example 2 Sanguinarine

Eight-week-old male C57BL6/J mice (n=8 per group) were administered sanguinarine (5 mg/kg/day, daily for 28 days, oral administration). A product available from SSX (Cat. No. 1845, Sanguinarine Chloride 10 mg) was used as sanguinarine. A preparation method for a test solution for a treatment group was as follows: sanguinarine was first dissolved at 100 µg/µl in 100% DMSO and the solution was further dissolved in phosphate buffered saline (PBS) so that the final concentration of sanguinarine was 1 µg/µl. A test solution for a control group was prepared by dissolving DMSO at the same concentration in PBS (1% DMSO).

From the test starting day, the mice were bred under a 10% $O_2$ hypoxic environment to generate a hypoxia-induced pulmonary hypertension mouse model. From the same day, the test solutions for the control group and the treatment group were directly administered into the stomachs of the mice once daily through the use of a probe for mice. Regarding doses, the mice were measured for their body weights daily during a test period, and doses were calculated separately for the mice so as to achieve 5 mg/kg/day.

An administration period (=hypoxic breeding period) was 28 days.

Figure 3:
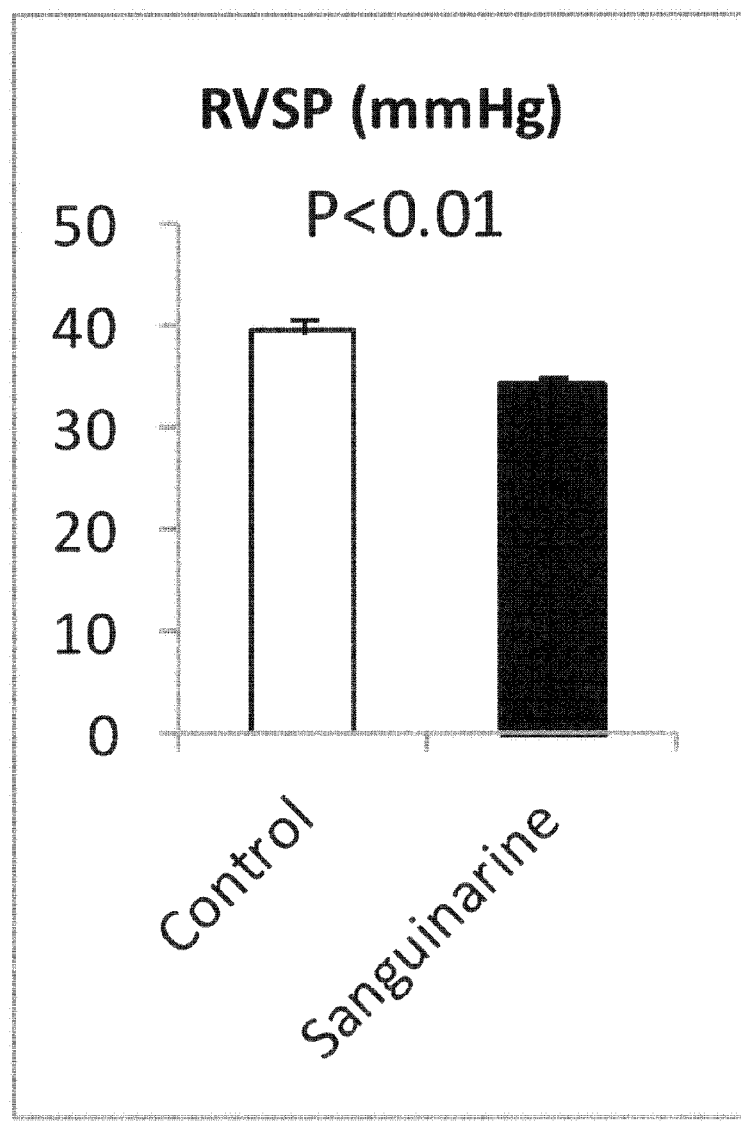
FIG. 3 is a graph for showing the measurement results of right ventricular systolic pressure in Example 2.
Figure 4:
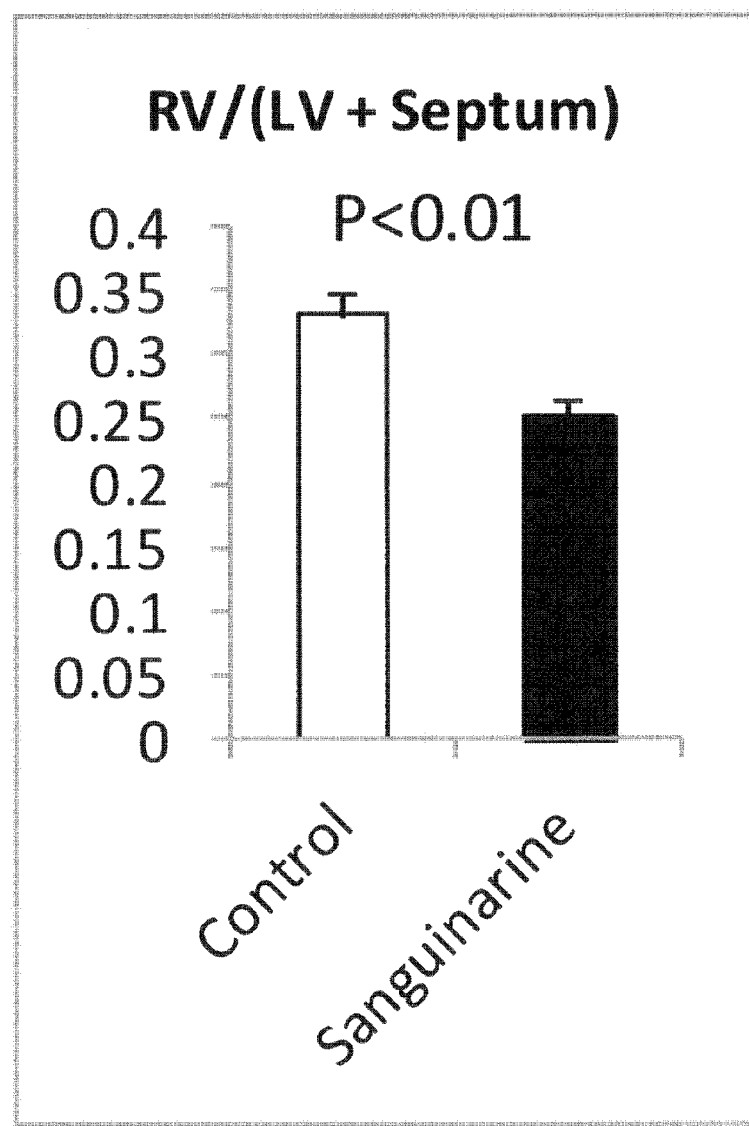
FIG. 4 is a graph for showing the ratios of right ventricular free wall weight to left ventricle plus septum weight in Example 2.
Figure 5:
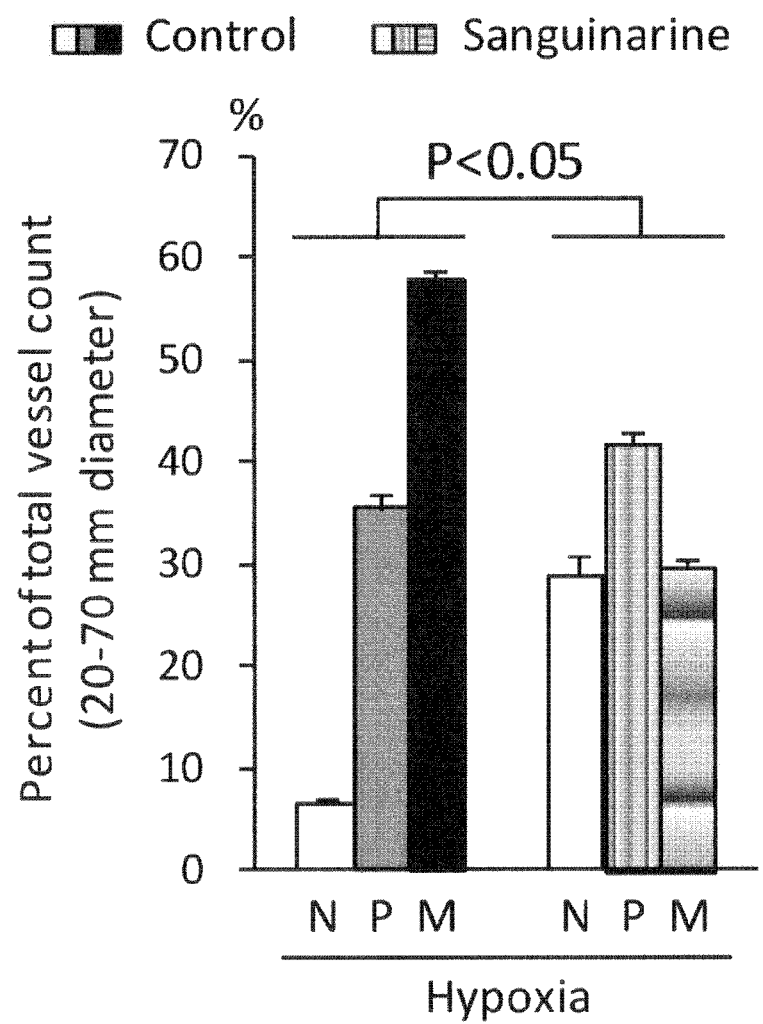
FIG. 5 is a graph for showing the results of staining for α-smooth muscle actin in Example 2.

After daily administration for 28 days, pulmonary hemodynamics and right ventricular hypertrophy were assessed at the end point (on day 28 after the start of hypoxic stimulation). The assessment of pulmonary hemodynamics was performed by directly measuring right ventricular systolic pressure (RVSP) with a pressure measurement catheter (Transonic Scisense) inserted into the right jugular vein. In addition, the assessment of right ventricular hypertrophy was performed by measuring right ventricular free wall (RV) weight in a dissected heart tissue to calculate its ratio to left ventricle plus septum (LV+Septum) weight (RV/(LV+Septum)). RV/(LV+Septum) serves as an indicator of right ventricular hypertrophy. A larger numerical value for RV/(LV+Septum) indicates a higher degree of right ventricular hypertrophy. The results are shown in FIG. 3 and FIG. 4. In addition, in order to assess pulmonary vascular remodeling, staining for α-smooth muscle actin (α-SMA) in a lung tissue section was performed on day 28. Pulmonary vascular remodeling was assessed by performing immunostaining for α-smooth muscle actin (α-SMA) in a lung tissue section and quantitatively assessing the extent of muscularization (classified into three stages, i.e., non-muscularization, partial muscularization, and full muscularization) of α-SMA-positive distal pulmonary arteries. Specifically, in each section, about 100 pulmonary arteries having diameters of from 20 µm to 70 µm were each assessed for a double elastic lamina. In this assessment, a pulmonary artery in which a double elastic lamina including an internal elastic lamina and an external elastic lamina was visible for less than 50% of the entire periphery of the pulmonary artery was considered non-muscularized, a pulmonary artery in which the double elastic lamina was visible for 50% or more and less than 100% of the entire periphery of the pulmonary artery was considered partially muscularized, and a pulmonary artery in which the double elastic lamina was visible throughout the entire periphery of the pulmonary artery was considered fully muscularized. The results are shown in FIG. 5. As shown in FIG. 5, the right ventricular systolic pressure and right ventricular hypertrophy in response to chronic hypoxic stimulation were found to be significantly reduced in the sanguinarine administration group as compared to the control group.

Example 3 Bufadienolide

Eight-week-old male C57BL6/J mice (n=8 per group) were administered cinobufotalin (5 mg/kg/day, daily for 28 days, intraperitoneal administration). A product available from Sigma (Cat. No. C1147-10MG, Cinobufotalin 10 mg) was used as cinobufotalin. A preparation method for a test solution for a treatment group was as follows: cinobufotalin was first dissolved at 30 µg/µl in 100% DMSO and the solution was further dissolved in PBS so that the final concentration of cinobufotalin was 0.3 µg/µl. A test solution for a control group was prepared by dissolving DMSO at the same concentration in PBS (1% DMSO). From the test starting day, the mice were bred under a 10% $O_2$ hypoxic environment to generate a hypoxia-induced pulmonary hypertension mouse model. From the same day, daily intraperitoneal administration of the test solutions for the control group and the treatment group was started. Regarding doses, the mice were measured for their body weights daily during a test period, and doses were calculated separately for the mice so as to achieve 5 mg/kg/day.

An administration period (=hypoxic breeding period) was 28 days.

After daily administration for 28 days, pulmonary hemodynamics and right ventricular hypertrophy were assessed at the end point (on day 28 after the start of hypoxic stimulation). In addition, in order to assess pulmonary vascular remodeling, staining for α-smooth muscle actin (α-SMA) in a lung tissue section was performed on day 28. The same techniques as those of Example 2 were used for specific measurement and assessment of pulmonary hemodynamics and right ventricular hypertrophy.

Figure 6:
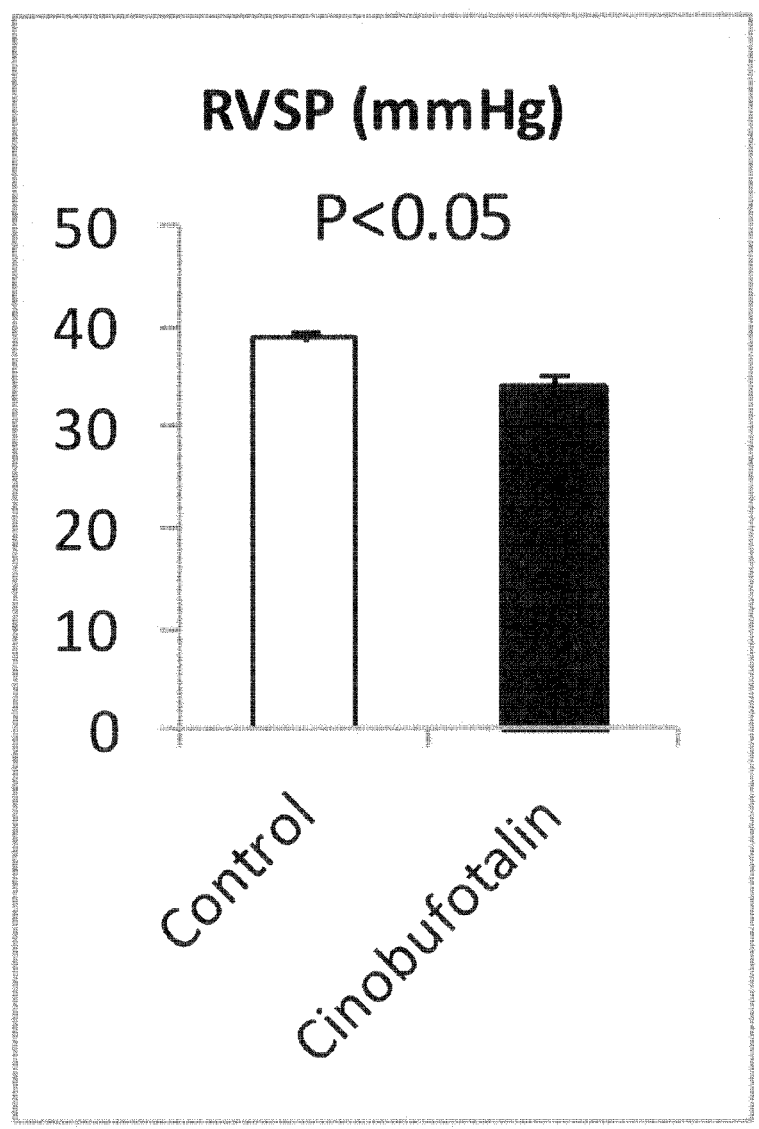
FIG. 6 is a graph for showing the measurement results of right ventricular systolic pressure in Example 3.
Figure 7:
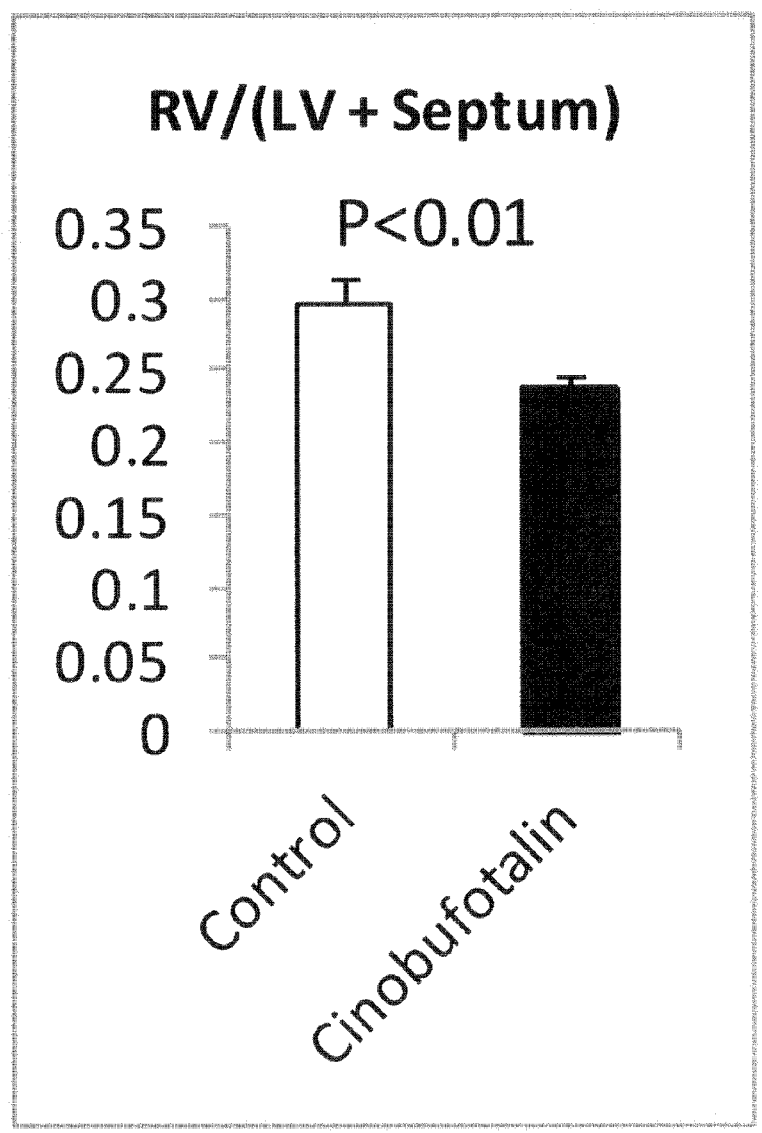
FIG. 7 is a graph for showing the ratios of right ventricular free wall weight to left ventricle plus septum weight in Example 3.

The results are shown in FIG. 6 and FIG. 7. As shown in FIG. 6 and FIG. 7, the right ventricular systolic pressure and right ventricular hypertrophy in response to chronic hypoxic stimulation were found to be significantly reduced in the cinobufotalin administration group as compared to the control group.

Example 4 Pristimerin

Eight-week-old male C57BL6/J mice (n=8 per group) were administered pristimerin (1 mg/kg/day, on alternate days for 28 days, intraperitoneal administration). A product available from RSD (Cat. No. 3731/50, Pristimerin 50 mg) was used as pristimerin. A preparation method for a test solution for a treatment group was follows: pristimerin was first dissolved at 6 µg/µl in 100% DMSO and the solution was further dissolved in PBS so that the final concentration of pristimerin was 0.06 µg/µl. A test solution for a control group was prepared by dissolving DMSO at the same concentration in PBS (1% DMSO).

From the test starting day, the mice were bred under a 10% $O_2$ hypoxic environment to generate a hypoxia-induced pulmonary hypertension mouse model. From the same day, alternate-day intraperitoneal administration of the test solutions for the control group and the treatment group was started. Regarding doses, the mice were measured for their body weights daily during a test period, and doses were calculated separately for the mice so as to achieve 1 mg/kg/day.

An administration period (=hypoxic breeding period) was 28 days.

After alternate-day administration for 28 days, pulmonary hemodynamics and right ventricular hypertrophy were assessed at the end point (on day 28 after the start of hypoxic stimulation). In addition, in order to assess pulmonary vascular remodeling, staining for α-smooth muscle actin (α-SMA) in a lung tissue section was performed on day 28. The same techniques as those of Example 2 were used for specific measurement and assessment of pulmonary hemodynamics and right ventricular hypertrophy.

Figure 8:
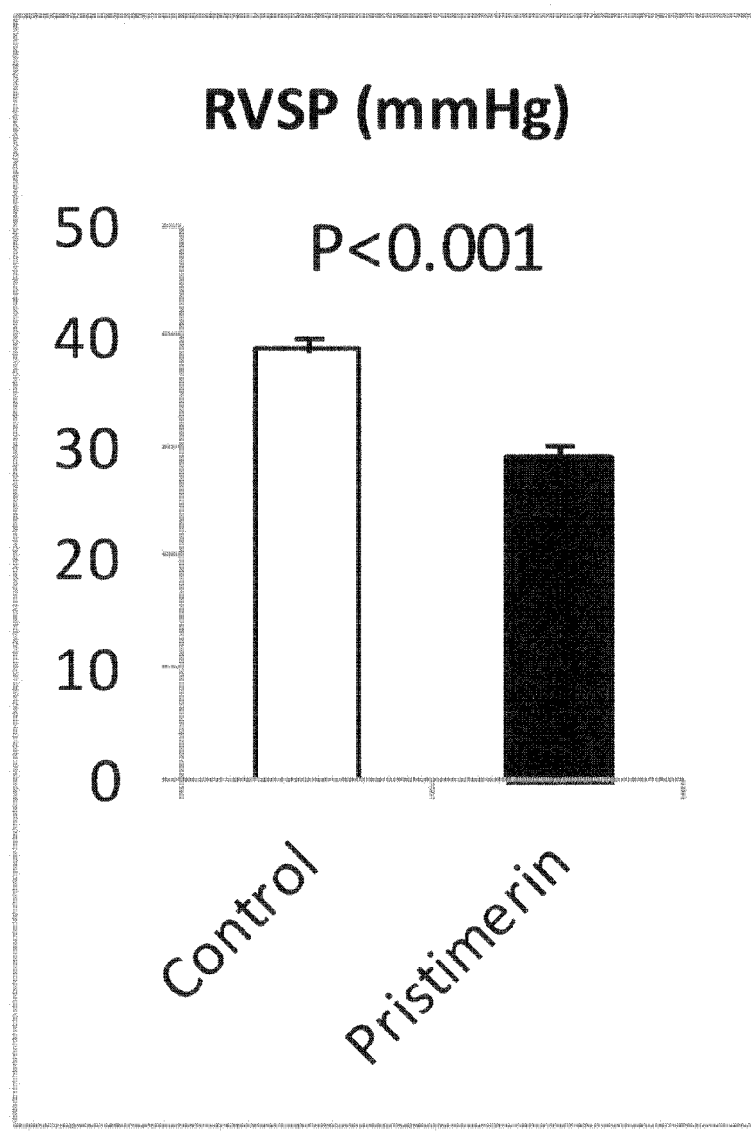
FIG. 8 is a graph for showing the measurement results of right ventricular systolic pressure in Example 4.
Figure 9:
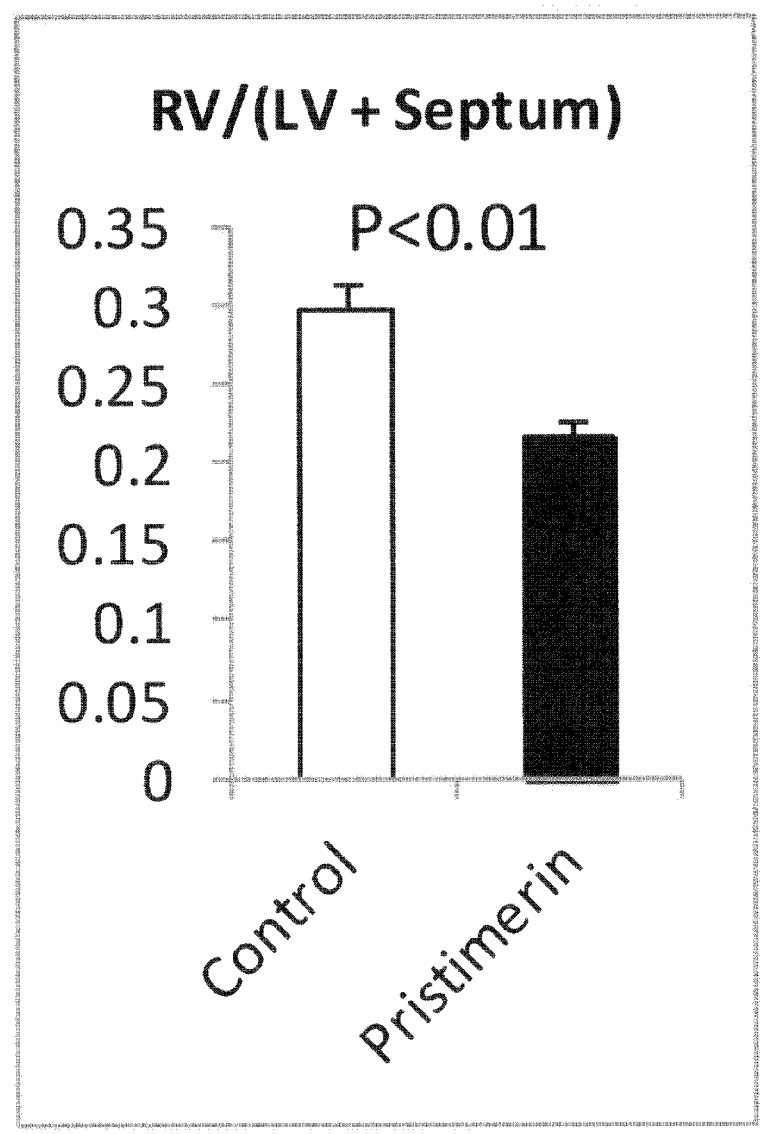
FIG. 9 is a graph for showing the ratios of right ventricular free wall weight to left ventricle plus septum weight in Example 4.

The results are shown in FIG. 8 and FIG. 9. As shown in FIG. 8 and FIG. 9, the right ventricular systolic pressure and right ventricular hypertrophy in response to chronic hypoxic stimulation were found to be significantly reduced in the pristimerin administration group as compared to the control group.

Example 5 Sanguinarine

In order to further assess the therapeutic effect of sanguinarine on pulmonary arterial hypertension (PAH), another pulmonary hypertension animal model was used. A specific procedure is as follows:

Method

Animal Test

In this test, littermates or vehicle treatment groups were used as controls. A Sugen/hypoxia-induced hypertension rat model was used to assess pulmonary hypertension (PH) (Non-patent Literature 4). In order to assess the development of pulmonary hypertension, right ventricular systolic pressure (RVSP) and right ventricular hypertrophy (RVH) were measured (Non-patent Literatures 4 to 6).

For right heart catheterization, a 1.4-F (for rats) pressure measurement catheter (Transonic Scisense) was inserted into the right jugular vein and advanced into the right ventricle to measure RVSP (Non-patent Literature 7).

In the Sugen/hypoxia model, rats (Sprague-Dawley, male, 7- to 10-week-old) were injected subcutaneously with a VEGF-receptor inhibitor SU5416 (Sigma-Aldrich, St Louis, Mo.) (20 mg per kg body weight) under isoflurane anesthesia and were then exposed to hypoxia (10% $O_2$) for 3 weeks. After the indicated period of treatment below, the rats were anesthetized with isoflurane (1.5%) to perform right heart catheterization. All data were analyzed using the PowerLab data acquisition system (AD Instruments, Bella Vista, Australia) and were averaged over 50 sequential beats (Non-patent Literatures 4 to 6). Serum samples were collected from the inferior vena cava in rats under anesthesia and centrifuged for 10 min at 2,500 g two times; protease inhibitor cocktail (Sigma-Aldrich) was added and aliquots were immediately stored at −80° C.

Assessment of Right Ventricular Hypertrophy

Formaldehyde-fixed dry hearts were dissected and the right ventricular free wall (RV) was removed from the left ventricle (LV) and septum. The ratio of right ventricular free wall (RV) weight to left ventricle plus septum (LV+Septum) weight [RV/(LV+S)] was measured to assess the extent of RVH (Non-patent Literature 4).

Sanguinarine Treatment in Rats with Sugen/Hypoxia-Induced PH

Rats (Sprague-Dawley, male, 7- to 10-week-old) were injected subcutaneously with a VEGF-receptor inhibitor SU5416 (Sigma-Aldrich) (20 mg per kg body weight) under isoflurane anesthesia and were then exposed to hypoxia (10% $O_2$) for 3 weeks (hypoxia+SU5416). On day 21, the rats were randomized to be orally administered sanguinarine (5 mg per kg body weight) or vehicle under normoxia (21% $O_2$) for 4 weeks. The vehicle administration group is expressed as vehicle controls. In addition, rats injected with saline on day 1 and exposed to normoxia for 7 weeks were used as (normoxic) controls. There were no significant differences in body weight and food consumption between the sanguinarine group and the vehicle control group. On day 49, the rats were anesthetized with isoflurane (1.0%) to measure RVSP, RVH, and pulmonary vascular remodeling. Thus, the development of PH was assessed.

Results

The rats were exposed to chronic hypoxia and the VEGF-receptor inhibitor SU5416 for 21 days (FIG. 10A). In the Sugen/hypoxia rat model, the sanguinarine treatment was started after the development of PH (FIG. 10A). The oral administration of sanguinarine for 28 days had no influence on the body weight or the food consumption (FIG. 10B). However, the RVSP and the RVH were reduced by the sanguinarine treatment as compared to the vehicle controls (FIG. 10C). In addition, protein levels of SeP in the lungs were elevated by the Sugen/hypoxia treatment (FIG. 10D). Meanwhile, SeP expression in the lungs was also significantly reduced by the sanguinarine treatment. As described above, sanguinarine ameliorated PH in the animal model in vivo.

Figure 10:
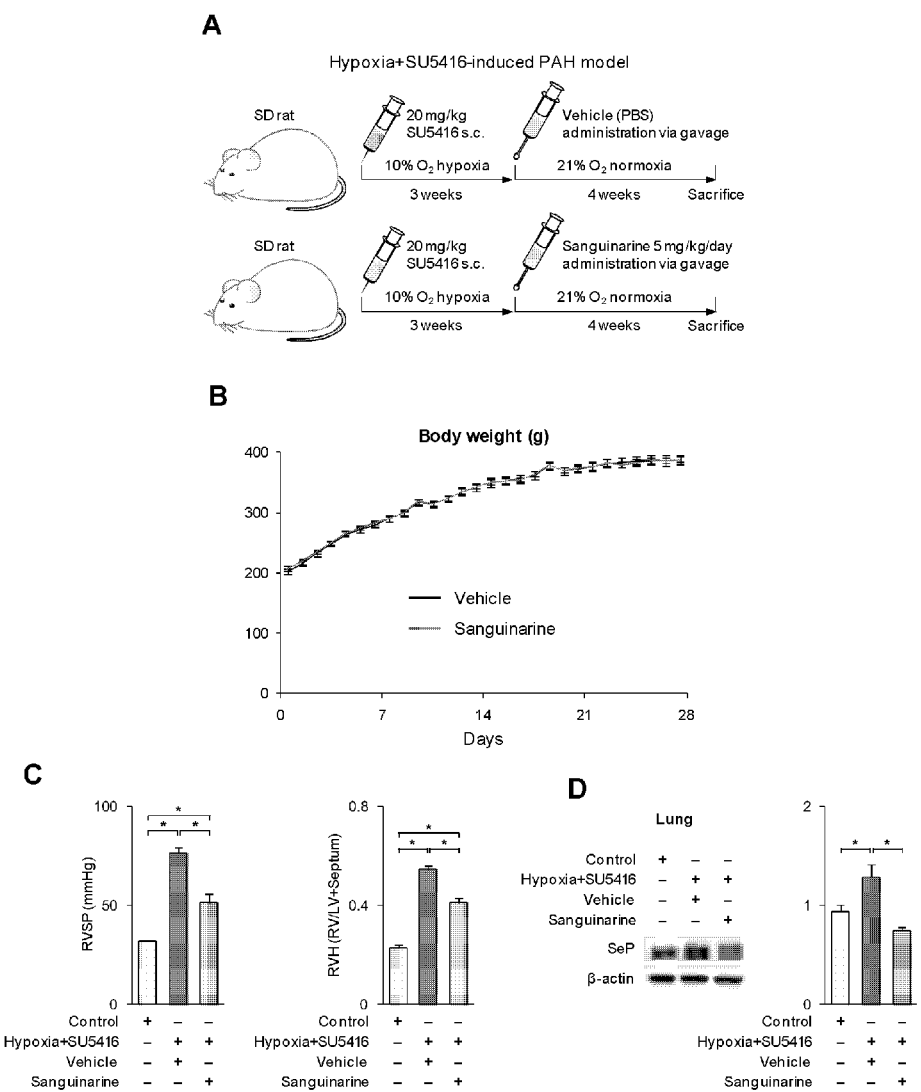
FIG. 10 are schematic protocols of tests in Example 5 or graphs and an image for showing the results of the tests.

The descriptions of FIG. 10 are as follows:

FIG. 10(A) is schematic protocols for sanguinarine administration to a Sugen/hypoxia rat model. Rats were exposed to a combination of chronic hypoxia (10% $O_2$) and a VEGF-receptor inhibitor SU5416 for 21 days, followed by oral administration of 5 mg/kg body weight sanguinarine or vehicle for 28 days.

FIG. 10(B) is a graph for showing the time-course of body weight from the starting point of administration of sanguinarine or vehicle for 4 weeks in Sugen/hypoxia rats (n=12). Data represent the mean±SEM.

FIG. 10(C) includes graphs for showing right ventricular systolic pressure (RVSP, left of FIG. 10(C)) and right ventricular hypertrophy (RVH, right of FIG. 10(C)) in rats exposed to chronic hypoxia and the VEGF-receptor inhibitor SU5416 for 21 days to induce PAH, followed by oral administration of vehicle and sanguinarine for 28 days. n=6 for (normoxic) control rats (rats that did not receive SU5416 injection nor chronic hypoxia), and n=12 for vehicle or sanguinarine-treated rats per group.

FIG. 10(D) includes an image and graph for showing quantification of SeP protein levels in normoxic control rats or hypoxia+SU5416 rats with or without sanguinarine treatment. Data represent the mean±SEM. *p<0.05. Comparisons of parameters were performed with one-way or two-way ANOVA and Tukey's HSD test for multiple comparisons.

The invention claimed is:

1. A method of treating pulmonary hypertension, comprising administering an effective dose of an ingredient having a selenoprotein P activity-inhibiting action to an animal, wherein the ingredient having a selenoprotein P activity-inhibiting action is selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a,14b tetradecahydropicene-2-carboxylate, or a salt thereof.

2. The method according to claim 1, wherein pulmonary hypertension is pulmonary arterial hypertension.

3. The method according to claim 1, wherein the ingredient having a selenoprotein P activity-inhibiting action is orally administered.

4. The method according to claim 2, wherein the ingredient having a selenoprotein P activity-inhibiting action is orally administered.

5. A method of inhibiting selenoprotein P activity, comprising administering an effective dose of at least one kind selected from the group consisting of sanguinarine, bufadienolide, and methyl 10-hydroxy-2,4a,6a,9,12b,14a-hexamethyl-11-oxo-1,2,3,4,4a,5,6,6a,11,12b,13,14,14a,14b-tetradecahydropicene-2-carboxylate to an animal.

* * * * *